US008097756B2

(12) United States Patent  (10) Patent No.: US 8,097,756 B2
Tu et al.  (45) Date of Patent: Jan. 17, 2012

(54) PROCESS FOR PRODUCING CARBOXYLIC ACID ANHYDRIDES

(75) Inventors: Ching Liang Tu, Tainan County (TW); Chia Hui Shen, Kaohsiung County (TW); Chia Jung Tsai, Kaohsiung (TW); Chi He Chen, Kaohsiung County (TW)

(73) Assignee: China Petrochemical Development Corporation, Taipei (TW)

( * ) Notice: Subject to any disclaimer, the term of this patent is extended or adjusted under 35 U.S.C. 154(b) by 218 days.

(21) Appl. No.: 12/370,268

(22) Filed: Feb. 12, 2009

(65) Prior Publication Data

US 2010/0145098 A1  Jun. 10, 2010

(30) Foreign Application Priority Data

Dec. 4, 2008  (TW) .............................. 97147075 A

(51) Int. Cl.
*C07C 51/54* (2006.01)
(52) U.S. Cl. ........................................................ 562/891
(58) Field of Classification Search ........................ None
See application file for complete search history.

(56) References Cited

U.S. PATENT DOCUMENTS

| | | | |
|---|---|---|---|
| 3,689,533 | A | 9/1972 | Schultz |
| 3,717,670 | A | 2/1973 | Schultz |
| 4,002,678 | A | 1/1977 | Naglieri et al. |
| 4,115,444 | A | 9/1978 | Rizkalla |
| 4,333,884 | A | 6/1982 | Kubbeler et al. |
| 4,335,059 | A | 6/1982 | Rizkalla |
| 4,430,273 | A | 2/1984 | Erpenbach et al. |
| 4,544,511 | A | 10/1985 | Isshiki et al. |
| 4,906,415 | A | 3/1990 | Luft et al. |
| 5,298,586 | A | 3/1994 | Beevor et al. |
| 5,488,143 | A | 1/1996 | Uhm et al. |
| 6,916,951 | B2 | 7/2005 | Tustin et al. |

FOREIGN PATENT DOCUMENTS

| | | |
|---|---|---|
| CN | 1778468 | 5/2006 |
| CN | 1876239 | 12/2006 |
| EP | 0 391 680 | 10/1990 |

OTHER PUBLICATIONS

Ionic liquid structure effect upon reactivity of toluene carbonylation: 1. Organic cation structure; Ernesto J. Angueira et al.; School of Chemical and Biomolecular Engineering, Atlanta, GA; 2005 Elwevier B.V.
Ionic Liquids in catalysis by Tom Welton; Dept. of Chemistry, Imperial College of Science, South Kensington, London; 2004 Published by Elsevier B.V.
Ionic Liquids: applications in catalysis; Dongbin Zhao et al.; College of Chemistry and Molecular Engineering, Peking University, Beijing China; 2002 Elsevier Science B.V.

*Primary Examiner* — Paul A Zucker
(74) *Attorney, Agent, or Firm* — Woodard, Emhardt, Moriarty, McNett & Henry LLP

(57) ABSTRACT

A process for producing carboxylic acid anhydrides by the carbonylation reaction of a carboxylic acid ester, derived from an alcohol and a carboxylic acid, with carbon monoxide containing a small amount of hydrogen in a liquid reaction medium in the presence of a Group VIII B catalyst to produce a carboxylic acid anhydride. The reaction medium comprises the Group VIII B catalyst, an organic halide, the carboxylic acid ester, an alkali metal salt, the carboxylic acid anhydride, the carboxylic acid, and at least one ionic liquid consisting of a cation and an anion where the cation of the ionic liquid has a nitrogen-containing heterocyclic structure. The ionic liquid has at least one of the following structural forms:

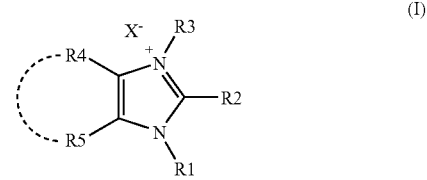

(I)

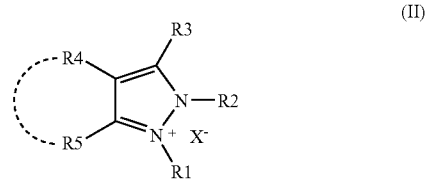

(II)

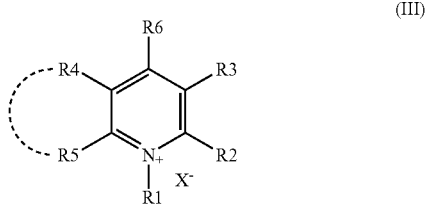

(III)

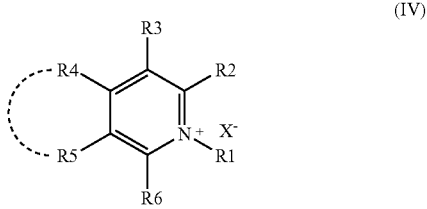

(IV)

The reaction rate of the carbonylation reaction is increased by the use of the specified ionic liquid promoters.

18 Claims, No Drawings

PROCESS FOR PRODUCING CARBOXYLIC ACID ANHYDRIDES

FIELD OF THE INVENTION

The present invention relates to a process for producing carboxylic acid anhydrides by the carbonylation reaction of a derivative from an alcohol and a carboxylic acid with carbon monoxide, and in particular, a process for producing acetic anhydride by the carbonylation reaction of methyl acetate with carbon monoxide. The characteristic thereof is that in a catalytic system containing a Group VIII B catalyst, one or more ionic liquids are added as the promoter to increase the reaction rate, so that the operational range for the reaction can be extended and the reaction can be carried out under milder conditions.

BACKGROUND OF THE INVENTION

Acetic anhydride is a well-known raw material widely used in the chemical industry, which is mainly used for producing chemicals such as cellulose acetate and is an important raw material for synthesizing medicines, flavors, dyes, etc. There are currently three industrial processes for producing acetic anhydride, including the ketone process, the acetaldehyde oxidation process and the methyl acetate carbonylation process.

The ketone process is carried out by dissociating one water molecule or methane from the raw material, acetic acid or acetone, at a high temperature to form ketone, which then reacts with acetic acid to form acetic anhydride. This process is carried out at a reaction temperature of up to 750° C. and thus will gradually go out of use in the future due to its high energy-consuming demand. The acetaldehyde oxidation process is carried out by oxidizing acetaldehyde into peracetic acid, in the presence of the metal catalyst such as manganese, cobalt, nickel, copper, etc., which further reacts with acetaldehyde to form acetic anhydride and the by-product, water. Acetic anhydride will further be hydrolyzed into acetic acid ant the yield of acetic anhydride will thus be reduced. Therefore, the product thereof is the mixture of acetic anhydride and acetic acid. The methyl acetate carbonylation process for producing acetic anhydride uses methyl acetate and carbon monoxide as the raw materials to produce acetic anhydride in the presence of transition metal catalysts and iodide promoter. Currently, the old-fashioned ketone process, which is small in scale and is adopted by many manufacturers, is predominant; however, for commercially producing acetic anhydride in large scale, the methyl acetate carbonylation process is used due to the high energy consuming and other drawbacks of the ketone process.

The methyl acetate carbonylation process for producing acetic anhydride is an expanded application of the methanol carbonylation process for producing acetic acid. The difference between the methyl acetate carbonylation process and the methanol carbonylation process is the water content of the reaction solution; the reaction solution of the former has to be kept in anhydrous conditions, while the reaction solution of the latter can have any water ratio of between 1 to 20 wt. %. Water has a great influence on the stability of the catalyst, and the high water content is advantageous to the stability of the catalyst. Therefore, the stability of the catalyst in the anhydrous system of the methyl acetate carbonylation process is a primary problem that should be overcome. In order to solve the problem, a promoter or a co-catalyst such as alkali metal, phosphonium salt, ammonium salt and transition metal catalysts can be added to promote the stability and activity of the catalytic system. In addition, in the methyl acetate carbonylation process for producing acetic anhydride, a small amount of hydrogen must be added in the carbon monoxide feed gas; the presence of hydrogen can reduce the trivalent rhodium $[Rh(CO)_2I_4]^-$ in the catalytic system to a univalent rhodium $[Rh(CO)_2I_2]^-$ having the activity, so as to maintain the activity of the rhodium catalyst. However, an overhigh hydrogen concentration will increase the production of the by-products of vinyl acetate, diacetate and acetone. Currently, all of the researches on methyl acetate carbonylation process mainly focus on the maintenance of the catalyst stability under an anhydrous system, the decrease of corrosiveness to equipments and the increase of the catalytic efficiency. In numerous catalyst researches, the Group VIIIB metals are mostly preferentially chosen for the active metal, and the metal catalysts such as rhodium, iridium, ruthenium, cobalt, nickel etc. have been much studied, of which the rhodium catalyst [U.S. Pat. No. 4,430,273, U.S. Pat. No. 4,333,884 and U.S. Pat. No. 5,298,586] and the nickel catalyst [U.S. Pat. No. 4,002,678, U.S. Pat. No. 4,906,415, U.S. Pat. No. 4,335,059 and U.S. Pat. No. 4,544,511] are most widely studied. The selectivity of them both can be higher than 95%, but the activity of rhodium is ten times or above that of nickel. Therefore, the rhodium catalytic system is mainly used in the current industrial processes.

The addition of one or more promoters into the catalytic system to improve and increase the catalytic efficiency of the catalyst is the most important subject in these researches. U.S. Pat. No. 4,002,678 discloses that under an anhydrous condition, a carbonylation reaction is carried out by using nickel and chromium as the catalyst and carbon monoxide and methyl acetate or dimethyl ether as the raw materials in the presence of a halide and a trivalent organo-nitrogen compound or a trivalent organo-phosphorus compound. EP0391680A1 discloses a process for preparing a carboxylic acid by using an alcohol or its ester under a water-containing condition, in which a quaternary ammonium iodide is used as a stabiliser of the rhodium catalyst. U.S. Pat. No. 4,115,444 discloses a process for preparing acetic anhydride, in which a Group VIIIB noble metal is used as the catalyst, together with multiple promoters comprising at least one metal of Groups IVB, VB, and VIB or a non-noble metal of Group VIIIB, or their compounds and a trivalent organo-nitrogen compound or a trivalent organo-phosphorus compound; the catalyst thereof is rhodium and iridium, the metal promoter is iron, cobalt, nickel, chromium, etc., and the organo-nitrogen compound promoter includes an amine, an imidazole, an imide, an amide, an oxime, etc. CN 1876239A and CN 1778468A both disclose a catalytic system for the synthesis of the carbonyl group of methyl acetate to an acid anhydride by using a rhodium compound as the catalyst and different contents of alkyl iodides, hetero-polyacid salts and alkali metal iodine salts as the promoter; the performance of this catalytic system is improved by the synergistic effect of the hetero-polyacid salts and the catalyst. In the carbonylation process of Taiwan Application No. 97100527, different nitrogen-containing heterocyclic organic promoters are used to form with the rhodium catalyst a stabilized complex, which has the effect of promoting the carbonylation reaction rate; the addition of these organic promoters can lower the reaction temperature or decrease the amount of lithium iodide to be added but maintain the original reaction rate, which has the effect of saving energy and reducing production cost.

Ionic liquids are currently the newest research subject. Due to their characteristic of low vapor pressure, ionic liquids are easily separated and recovered in a catalytic system [Catal. Today, 2002, 74, 157-189] and have good thermal stability, chemical stability, ionic conductivity and polarization potential and thus can be used as an environment-friendly solvent. Therefore, ionic liquids are paid more and more attention to [Chem. Rev, 2004, 248, 2459-2477]. Ionic liquids can play various roles in a catalytic reaction as an organic catalyst, a co-catalyst, the source of a ligand, or the solvent for the reaction [Coordination Chemistry Review 248 (2004) 2459-2477] with certain effects. U.S. Pat. No. 3,689,533 discloses a process for the preparation of acetic acid by the gas-solid phase methanol carbonylation process in the presence of a rhodium-supported catalyst and a halide promoter. However, because the thermal conductivity of gas is extremely smaller than that of liquid, the major problem of the gas phase carbonylation process conducted by using a solid catalyst lies in the removal of reaction heat [U.S. Pat. No. 5,488,143, U.S. Pat. No. 3,717,670 and U.S. Pat. No. 3,689,533]. U.S. Pat. No. 6,916,951 B2 uses a non-volatile ionic liquid as the solvent with a rhodium catalyst dissolved therein to solve the problem of the heat removal in a heterogeneous phase carbonylation process by the participation of the ionic liquid.

There exists so close relation between the organic cation and anion of an ionic liquid that the designing of the structure of ionic liquids greatly influence the process of electron transport and the physical properties of ionic liquids. White et al. [Journal of Molecular Catalysis A: Chemical 238 (2005) 163-174] further verifies that the structure of ionic liquids in the carbonylation reaction will affect the solubility of CO and promote the catalytic performance of active species, and will further affect the stability of the whole reaction system. U.S. Pat. No. 5,298,586 and U.S. Pat. No. 4,430,273 both clearly disclose that the addition of quaternary nitrogen-containing ionic iodides in the rhodium-catalyzed carbonylation process under anhydrous conditions to produce carboxylic acid anhydrides can effectively improve the stability and solubility of rhodium catalysts. In addition to keeping the stability of rhodium catalysts, the promotion of catalytic efficiency is also a goal to be sought. Therefore, developing a process of producing acetic anhydrides which can effectively stabilize rhodium catalysts and maintain a high reaction rate under severe carbonylation conditions is still a main research subject in the future.

SUMMARY OF THE INVENTION

The object of the present invention is to provide a process for producing carboxylic acid anhydrides, of which the catalytic performance can be promoted and the productivity can be increased under anhydrous conditions.

In order to achieve the aforementioned and other objects, the present invention provides a process for producing carboxylic acid anhydrides by the carbonylation reaction of a carboxylic acid ester, derived from an alcohol and a carboxylic acid, with carbon monoxide containing a small amount of hydrogen in a liquid reaction medium in the presence of a Group VIII B catalyst to produce a carboxylic acid anhydride. The reaction medium comprises the Group VIII B catalyst, an organic halide, the carboxylic acid ester, an alkali metal salt, the carboxylic acid anhydride, the carboxylic acid, and at least one ionic liquid consisting of a cation and an anion where the cation of the ionic liquid has a nitrogen-containing heterocyclic structure. The process of the present invention mainly uses the promoter and ionic liquid to increase the activity of the catalyst and further promote the catalytic performance, and thus has the effects of promoting the reaction rate and increasing the productivity.

According to the process of the present invention, the liquid catalytic system as used includes at least one ionic liquid, which consists of a cation and an anion where the cation has a nitrogen-containing heterocyclic structure such as 5- or 6-membered heterocyclic cation having 1 or 2 nitrogen atoms.

Specifically, the ionic liquid is selected from at least one structure of the following structural forms (I) to (IV):

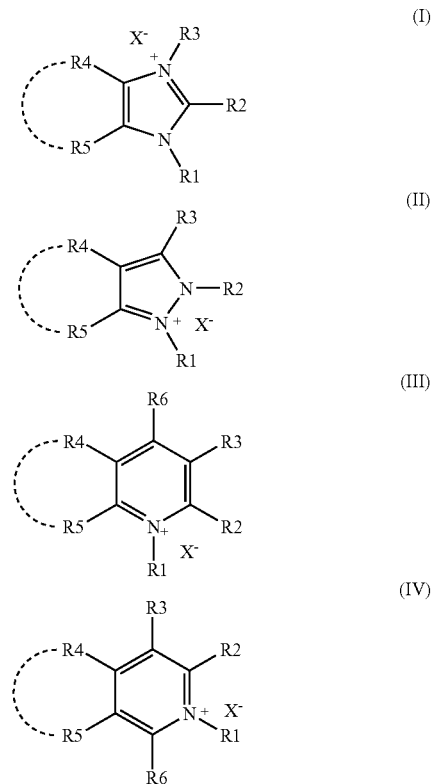

in which R1~R6 can be the same or different and are independently selected from the group consisting of hydrogen atom, $C_{1-12}$ alkyl group, $C_{3-12}$ cycloalkyl group, $C_{6-20}$ aryl group, $C_{7-20}$ alkylaryl group, $C_{7-20}$ arylalkyl group, hydroxyl group, $C_{1-12}$ alkylhydroxyl group, carboxyl group, $C_{2-12}$ carboxyalkyl group, $C_{1-12}$ aminoxy group (—O—NRR'), $C_{2-12}$ alkoxyformyl group (—CO—OR), $C_{2-12}$ alkyacyloxy group (—O—CO—R), $C_{1-12}$ aminoformyl group (—CO—NRR'), $C_{2-12}$ alkylamido group (—NR—CO—R) □$C_{1-12}$ alkylamino group, $C_{3-12}$ cycloalkylamino group, $C_{1-12}$ aminoalkyl group, $C_{4-12}$ cycloaminoalkyl group, $C_{2-12}$ alkylacyl group (—CO—R), $C_{3-12}$ cycloalkylaryl group, $C_{1-12}$ amidoalkyl group, $C_{1-12}$ imido group, $C_{1-12}$ imidoalkyl group, $C_{1-12}$ alkoxy group (—O—R), $C_{3-12}$ cycloalkoxy group, $C_{1-12}$ amino acid alkyl group□ and R4 and R5 can be coupled to each other to form an aromatic ring, a heteroaromatic ring or a non-aromatic ring.

The anion constituting the ionic liquid includes, but is not limited to, $F^-$, $Cl^-$, $Br^-$, $I^-$, $PF_6^-$, $SCN^-$, $HSO_4^-$, $CH_3SO_3^-$, $CH_3SO_4^-$, $AlCl_4^-$, $Al_2Cl_7^-$, $Al_3Cl_{10}^-$, $CH_3CH_2SO_4^-$ and $BF_4^-$, and is preferably selected from $Cl^-$, $Br^-$, $I^-$.

In the process for producing carboxylic acid anhydrides according to the present invention, the carbonylation reaction of a carboxylic acid ester, derived from an alcohol and a carboxylic acid, with carbon monoxide containing a small amount of hydrogen are carried out in the presence of a catalyst (for example, rhodium (Rh)) in a reaction vessel to produce a carboxylic acid anhydride. The alcohol is an aliphatic alcohol compound having 1-6 carbon atoms, and the carboxylic acid is a carboxylic acid having 1-6 carbon atoms. According to the process of the present invention, an adequate amount of hydrogen, preferably at a concentration of 10% or below, is contained in the carbon monoxide gas for the carbonylation reaction, which can facilitate the maintenance of the activity of the Rh catalyst. In the liquid reaction medium, 300-5000 ppm of the Rh catalyst, 5-30 wt. % of the organic halide, 1-15 wt. % of the alkali metal salt, 0.1 wt. % or above of the ionic liquid, and the carboxylic acid ester, the carboxylic acid anhydride, the carboxylic acid and a small amount of impurities are usually contained. The ionic liquids as used in the process of the present invention can not only mitigate the danger of volatile solvents, but also promote the activity of the catalyst and improve the reaction selectivity and productivity. From the viewpoint of productivity, the carbonylation reaction is usually carried out at a temperature of between 160-240° C. and at a pressure of between 20-60 $kg/cm^2$.

Compared with the aforementioned prior art, the process of the present invention uses different ionic liquids as the promoter, which can form a stable complex compound with the Rh catalyst and has the effect of promoting the carbonylation reaction rate. The addition of alkali metal iodine salts in the conventional anhydrous carbonylation process has the effect of stabilizing rhodium, but on the other side causes much trouble in the subsequent processes of purification, separation and deiodination of the product. The addition of ionic liquids can promote the carbonylation reaction rate and reduce the subsequent operation of the equipment for the deiodination process, which has the advantage of reducing the cost of purifying the acetic anhydride product.

DESCRIPTION OF PREFERRED EMBODIMENTS

The features and effects of the present invention will be further explained with reference to the preferred embodiments below, which are, however, not intended to restrict the scope of the present invention.

The present invention may be operated as a batch process, in which the equipment as used mainly includes, for example, a 0.5-liter reactor and a carbon monoxide storage tank both made of anticorrosive materials. The reactor itself is provided with a speed-change motor capable of controlling the rotational speed, which can be appropriately adjusted so as to maintain a vapor/liquid well-mixing effect. The inside and the outside of the reactor are provided with a cooling coil and an electrically heating plate, respectively, so as to control and maintain a stable reaction temperature. A pressure control valve is provided between the reactor and the hydrogen and carbon monoxide storage tanks so as to maintain and control the pressure of the main reactor.

One preferred embodiment of the present invention is to produce acetic anhydride by carrying out the carbonylation reaction of methyl acetate with carbon monoxide containing a small amount of hydrogen in the reactor. The reaction medium in the reactor for carrying out the carbonylation reaction is maintained to comprise a Group VIII B catalyst such as, for example, rhodium; a carboxylic ester derived from an alcohol and a carboxylic acid such as, for example, methyl acetate, or an ether derived from an alcohol compound such as, for example, dimethyl ether; an organic halide corresponding to the raw material of alcohol, such as, for example, methyl iodide; an alkali metal salt such as, for example, lithium iodide; a carboxylic acid anhydride such as, for example, acetic anhydride; a carboxylic acid such as, for example, acetic acid; and at least one ionic liquid consisting of a cation and an anion.

The carbon monoxide feed gas in the carbonylation process contains an adequate amount of hydrogen, which can maintain the activity of the Rh catalyst. Preferably, the carbon monoxide feed gas contains hydrogen at a concentration of 10% or below. In the liquid reaction medium, 300-5000 ppm of the Rh catalyst, 5-30 wt. % of organic halide, 1-15 wt. % of alkali metal salt, 0.5-20 wt. % of ionic liquid, and the carboxylic acid ester, carboxylic acid anhydride, carboxylic acid and a small amount of impurities are usually contained. The carbonylation reaction can be carried out under the condition of temperatures of 160-240° C. and CO controlled pressures of 20-60 $kg/cm^2$.

Alternatively, the present invention can be operated as a continuous process. Another preferred embodiment of the present invention is to continuously feed the raw material of methyl acetate, together with carbon monoxide containing a small amount of hydrogen, into the carbonylation reactor and react methyl acetate with carbon monoxide so as to form acetic anhydride. The liquid reaction medium in the reactor comprises the Rh catalyst, methyl acetate, acetic acid, acetic anhydride, methyl iodide, an alkali metal salt and at least one ionic liquid promoter. Corresponding to the continuously feeding reactor, the reaction product effluent comprises the product of acetic anhydride and the unreacted methyl acetate, acetic acid, methyl iodide, Rh catalyst, alkali metal salt and organic promoter. The liquid reaction product is continuously outputted to a flash tank (or an evaporator), the light constituents of the liquid reaction product are evaporated and discharged from the top of the flash tank to the purifying zone to further separate acetic acid and acetic anhydride, and the Rh catalyst and other heavy constituents at the bottom of the flash tank are reflowed to the reactor. After the product of acetic anhydride is separated in the purifying zone, acetic acid and other constituents (including methyl iodide, methyl acetate, etc.) are reflowed to the reactor. During the reaction process, methyl iodide, the alkali metal salt and the ionic liquid promoter will not be consumed but are continuously circulated from the flash tank or the purifying zone to the reactor. If necessary, persons skilled in the art can consider adjusting the contents of the constituents of the reaction medium in accordance with the real operation situation.

Comparative Example 1

In this comparative example, a batch process without adding the ionic liquids of the present invention was used, as a comparative experiment, to carry out the carbonylation reaction. The total weight of the reaction solution was 350 g in which the following constituents were contained: 45 wt. % of methyl acetate, 20 wt. % of methyl iodide, 3 wt. % of acetic anhydride, lithium iodide (40000 ppm of Li ion), 700 ppm of the Rh catalyst, and an appropriately balanced amount of acetic acid as a solvent. The reactor into which the mixture of the aforementioned reactants had been fed was firstly pressurized with hydrogen to 1 $kg/cm^2$, and then carbon monoxide was introduced into the reactor, followed by a gradual elevation of temperature. After the set temperature for the reaction was reached, carbon monoxide was resupplied so that the inner pressure of the system reached 27 $kg/cm^2$. During the reaction, carbon monoxide kept on being resupplied with the consumption of carbon monoxide so that the pressure stably maintained 27 $kg/cm^2$. The consumption of carbon monoxide was recorded and a constituent analysis was carried out by sampling so as to calculate the unit space-time yield (STY) of acetic anhydride (unit: mole/liter*hour).

Examples 1-8

Improved Performance of Carbonylation Reaction Rate of Methyl Acetate (STY) by Addition of Different Ionic Liquids The carbonylation reactions were carried out under the same conditions as the Comparative Example 1, except that 0.07 mole of ionic liquid promoters were added in the reaction media. The results of the Examples 1-8 and the Comparative Example 1 were recorded in Table 1 where the Comparative Example 1 was a blank experiment that no ionic liquid promoter was added. It is obvious from Table 1 that the STY values for those having the ionic liquids added were all increased by 25% or above, which shows the addition of these kinds of ionic liquids according to the present invention indeed has the effect of promoting the carbonylation reaction rate.

TABLE 1

Influence of Addition of Ionic Liquids on Reaction Rate

| | Added Amount of ionic liquid | | STY value |
|---|---|---|---|
| | Reagents | Amount (mole) | (gmol/ L * hr) |
| Compar. Example 1 | ☐ | ☐ | 8.11 |
| Example 1 | 5-amino-1,3-dimethyl-1-phenylpyrazolium iodide | 0.07 | 10.21 |
| Example 2 | 2-amino-1-methylbenzimidazolium iodide | 0.07 | 10.49 |
| Example 3 | 1,2-dimethylbenzimidazolium iodide | 0.07 | 9.79 |
| Example 4 | N-methyl-4-di(methylamino)pyridinium iodide | 0.07 | 10.21 |
| Example 5 | N-methylquinolinium iodide | 0.07 | 10.35 |
| Example 6 | 1,4-dimethylquinolinium iodide | 0.07 | 10.63 |
| Example 7 | 4-amino-1,2-dimethylquinolinium iodide | 0.07 | 10.21 |
| Example 8 | 5-amino-1-methylisoquinolinium iodide | 0.07 | 10.91 |

Examples 9-10

Influence of Reaction Pressure and Ionic Liquids on Reaction Rate

The carbonylation reactions were carried out under the same conditions as the Comparative Example 1, except that 0.07 mole of the ionic liquid promoter, N-methylquinolinium iodide, was added in the reaction media and the CO pressure was altered. The experimental results were recorded in Table 2. It is obvious from Table 2 that the STY values of the carbonylation reaction could indeed be increased by adding the ionic liquid promoter. Also, increasing the reaction pressure could further increase the reaction rate. The reaction rate was not only obviously increased under high pressure, but also higher than the reaction rate of the Comparative Example 1 even under lower reaction pressure. Therefore, the present process can be applied to a lower pressure system with a less investment in equipment.

TABLE 2

Influence of Reaction Pressure and Ionic Liquids on Reaction Rate

| | Added Amount of Ionic Liquid | | | STY value |
|---|---|---|---|---|
| | Reagents | Amount (mole) | Pressure (kg/cm$^2$) | (gmol/ L * hr) |
| Compar. Example 1 | ☐ | | ☐ | 27 | 8.11 |
| Example 9 | N-methylquinolinium iodide | 0.07 | 24 | 9.23 |
| Example 5 | | | 27 | 10.49 |
| Example 10 | | | 33 | 11.05 |

Examples 11-13

Influence of Reaction Temperature and Ionic Liquids on Reaction Rate

The carbonylation reactions were carried out under the same conditions as the Comparative Example 1, except that 0.07 mole of the ionic liquid promoter, 2-amino-1-methylbenzimidazolium iodide, was added in the reaction media and the reaction temperature was altered. The experimental results were recorded in Table 3. It is obvious from Table 3 that the STY values of the carbonylation reaction could still be increased by adding the ionic liquid promoter and altering the reaction temperature, which shows the addition of these kinds of ionic liquid promoters according to the present invention indeed has the effect of promoting the carbonylation reaction rate at different reaction temperatures. In addition, when the Example 11 is compared with the Comparative Example 1, it is found that the addition of these kinds of ionic liquid promoters can maintain the original reaction rate at a lower reaction temperature, which has the effect of saving energy and reducing production cost.

TABLE 3

Influence of Reaction Temperature and Ionic Liquids on Reaction Rate

| | Added Amount of Ionic Liquid | | | STY value |
|---|---|---|---|---|
| | Reagents | Amount (mole) | Temp. (° C.) | (gmol/ L * hr) |
| Compar. Example 1 | ☐ | | ☐ | 190 | 8.11 |
| Example 11 | 2-amino-1-methylbenzimidazolium iodide | 0.07 | 180 | 8.25 |
| Example 2 | | | 190 | 10.49 |
| Example 12 | | | 200 | 10.63 |
| Example 13 | | | 210 | 11.19 |

Examples 14-15

Influence of Added Amount of Ionic Liquids on Reaction Rate

The carbonylation reactions were carried out under the same conditions as the Comparative Example 1, except that 0.07 mole, 0.10 mole and 0.15 mole of the ionic liquid promoters, N-methyl-4-di(methylamino)pyridinium iodide, were added in the reaction media. The experimental results were recorded in Table 4. It is obvious from Table 4 that the STY values of the carbonylation reaction were increased synchronously with the increase in the added amount of the ionic liquid promoter, which shows the carbonylation reaction rate can indeed be increased by the increase in the added amount of these kinds of ionic liquid promoters according to the present invention.

TABLE 4

Influence of Added Amount of Ionic Liquids on Reaction Rate

| Reagents | | Added Amount of Ionic Liquid | |
|---|---|---|---|
| | | Amount (mole) | STY value (gmol/L * hr) |
| Compar. Example 1 | ☐ | ☐ | 8.11 |
| Example 4 | N-methyl-4-di(methylamino)- pyridinium iodide | 0.07 | 10.21 |
| Example 14 | | 0.10 | 10.91 |
| Example 15 | | 0.15 | 13.01 |

While the present invention has been shown and described with reference to preferred embodiments thereof, it should not be considered as limited thereby. Various possible modifications and alterations could be conceived of by one skilled in the art to the form and the content of any particular embodiment, without departing from the scope of the present invention.

What is claimed is:

1. A process for producing carboxylic acid anhydrides by the carbonylation reaction of a carboxylic acid ester with carbon monoxide containing a small amount of hydrogen in a liquid reaction medium in the presence of a Group VIII B catalyst to produce a carboxylic acid anhydride, the carboxylic acid ester being derived from an alcohol and a carboxylic acid, and the reaction medium comprising the Group VIII B catalyst, an organic halide, the carboxylic acid ester, an alkali metal salt, at least one ionic liquid promoter, the carboxylic acid anhydride and the carboxylic acid; wherein the ionic liquid promoter is selected from:
   the group consisting of 5-amino-1,3-dimethyl-1-phenylpyrazolium iodide, 2-amino-1-methylbenzimidazolium iodide, 1,2-dimethylbenzimidazolium iodide, N-methylquinolinium iodide, N-methyl-4-di(methylamino)pyridinium iodide, 1,4-dimethylquinolinium iodide, 4-amino-1,2-dimethylquinolinium iodide and 5-amino-1-methylisoquinolinium iodide.

2. The process according to claim 1, wherein the anion is selected from $Cl^-$, $Br^-$ or $I^-$.

3. The process according to claim 1, wherein the alcohol is an alcohol having 1 to 6 carbon atoms.

4. The process according to claim 1, wherein the carboxylic acid is a carboxylic acid having 1 to 6 carbon atoms.

5. The process according to claim 1, wherein the carboxylic acid ester is methyl acetate.

6. The process according to claim 4, wherein the carboxylic acid is acetic acid.

7. The process according to claim 1, wherein the carboxylic acid anhydride is acetic anhydride.

8. The process according to claim 1, wherein the carbonylation reaction is carried out at a temperature of between 160 to 240° C.

9. The process according to claim 1, wherein the carbonylation reaction is carried out at a pressure of between 20 to 60 $kg/cm^2$.

10. The process according to claim 1, wherein the reaction medium contains the Group VIII B catalyst at a total concentration of 300 to 5000 ppm.

11. The process according to claim 10, wherein the Group VIII B catalyst is one or more catalysts selected from the group consisting of rhodium, nickel, cobalt and iridium.

12. The process according to claim 1, wherein the organic halide is a methyl halide.

13. The process according to claim 12, wherein the methyl halide is methyl iodide.

14. The process according to claim 13, wherein the reaction medium contains 5 to 30 wt. % of methyl iodide.

15. The process according to claim 1, wherein the carbon monoxide feed gas contains hydrogen at a concentration of 0.1 to 10%.

16. The process according to claim 1, wherein the alkali metal salt is a Group IA/IIA iodide salt.

17. The process according to claim 16, wherein the reaction medium contains 500 to 8000 ppm of Group IA/IIA metal ions for providing the corresponding content of iodine ions.

18. The process according to claim 1, wherein the ionic liquid promoter is added at a content of 0.1 wt. % or above.

* * * * *